United States Patent [19]

Haferkorn

[11] 4,017,520
[45] Apr. 12, 1977

[54] PRODUCTION OF MALEIC ANHYDRIDE BY AZEOTROPIC DEHYDRATION OF MALEIC ACID SOLUTIONS DERIVED FROM BENZENE OXIDATION PROCESSES

[75] Inventor: Herbert Haferkorn, Bottrop, Germany

[73] Assignee: Veba-Chemie AG, Gelsenkirchen-Buer, Germany

[22] Filed: Mar. 7, 1975

[21] Appl. No.: 556,240

[30] Foreign Application Priority Data

Mar. 8, 1974 Germany .......................... 2411101

[52] U.S. Cl. ....................................... 260/346.8 M
[51] Int. Cl.² ..................................... C07D 307/60
[58] Field of Search ............. 260/346.8 M; 203/15, 203/38, 61, 69

[56] References Cited

UNITED STATES PATENTS 2,340,490   2/1944   Porter ...................... 260/346.8 M

FOREIGN PATENTS OR APPLICATIONS 869,297   5/1961   United Kingdom ............ 260/346.8

*Primary Examiner*—Henry R. Jiles
*Assistant Examiner*—Bernard Dentz
*Attorney, Agent, or Firm*—Burgess, Dinklage & Sprung

[57] ABSTRACT

Maleic acid is recovered from aqueous solutions containing benzoquinone especially from a catalyst benzene oxidation process by:
 a. concentrating an aqueous maleic acid solution containing benzoquinone;
 b. adding from 0.1 to 2.0 weight percent of phthalic acid or its anhydride, based on the weight of maleic acid, to the concentrated solution from (a); thereafter
 c. separating the maleic acid from the mixture from (b) by continuous distillation with an organic solvent and purifying the separated maleic acid.

2 Claims, No Drawings

PRODUCTION OF MALEIC ANHYDRIDE BY AZEOTROPIC DEHYDRATION OF MALEIC ACID SOLUTIONS DERIVED FROM BENZENE OXIDATION PROCESSES

BACKGROUND

This invention relates to a process for recovering pure maleic acid from aqueous solutions containing benzoquinone especially those catalytic benzene oxidation processes.

The technical production of maleic anhydride is generally carried out by catalytic vapor phase oxidation of benzene or $C_4$-carbon atoms, as butene, butadiene and butane. The reaction gases occurring thereby are cooled after leaving the reactor such that maleic anhydride is condensed.

However, the separation temperature for the water in the reaction gases, must be kept considerably below the dew point, otherwise maleic anhydride is hydrated to maleic acid. At temperatures necessary for separation, mostly below 50° C, the vapor pressure of the maleic anhydride is such that considerable quantities of maleic acid remain in the waste gas.

To reduce losses these waste gases are then washed with water. A solution containing maleic acid results, called acid water, which can be concentrated up to 30 to 50 wt.% maleic acid. Maleic anhydride can be recovered from these acid waters for example by means of an organic solvent, mostly a technical xylene mixture. The acid waters are first dewatered and then the maleic acid is dehydrated to maleic anhydride.

At larger throughput, the dehydration is carried out in a continuously working dehydration column. Here the acid water is led to an xylene vapor stream in the column, whereby the evaporation and the dehydration heat are taken from the xylene stream under simultaneous use of the xylene as carrier stream for the azeotropic removal of water.

The column is filled for this purpose with Raschig rings or with suitable plates. The product from the sump of the dehydration column (maleic anhydride and xylene) is separated by distillation in a distillation column and afterwards the raw maleic anhydride is reworked in a further distillation to pure maleic anhydride.

The most important raw material for recovering maleic anhydride is benzene.

It is known that in continuously working dehydration columns, as far as they are fed with acid waters of benzene oxidation plants, black, tar-like precipitations occur which hamper the correct working of the column.

For avoiding these disadvantages, it was suggested to use distillation columns with column plates in which openings with movable valve plates adjusted in a cage are placed and whereby the openings are rounded to a venturi profile.

This means higher capital costs, for a dehydration column for avoiding of corrosion must be made at least partly of solid material.

This invention provides a chemical process for preventing the formation of such precipitations in the dehydration column. Examining the precipitations formed, it was found that the formation of water-insoluble precipitations can be prevented if a small quantity of benzoquinone is present in the acid water from the benzene oxidation plant. Benzoquinone occurs as by-product from the benzene oxidation. According to former experiences, the formation of benzoquinone cannot be wholly prevented. Benzoquinone occurs mainly in the acid water while in the maleic anhydride melt a small amount also appears. The acid waters often show benzoquinone quantities of 200 to 500 mg/l while higher contents are not uncommon.

Other impurities of the acid waters, like aldehydes, which usually exist in considerably higher concentrations (for example, 5 to 10 g/l acid water) do not form water insoluble precipitations in the dehydration column.

SUMMARY

It was found that the formation of tar-like water insoluble products in the dehydration column can be avoided by
a. concentrating an aqueous maleic acid solution containing benzoquinone;
b. adding from 0.1 to 2.0 weight percent of phthalic acid or its anhydride, based on the weight of maleic acid, to the concentrated solution from (a); thereafter
c. separating the maleic acid from the mixture from (b) by continuous distillation with an organic solvent and purifying the separated maleic acid.

DESCRIPTION

With the invention, a dehydration column can be conducted over considerably longer periods without a stagnation or purification being necessary. The added phthalic acid is also dehydrated in the column and finally becomes phthalic acid anhydride in the sump product, from which it can be regained distillatively for a renewed use in the acid waters. The quality of the pure maleic anhydride produced is not impaired. Also the throughput of existing apparatus is not affected by the invention. Also, apparatus changes of the known processes are not necessary.

The process of the invention is illustrated by the following examples:

EXAMPLE 1 (prior art)

For the continuous dehydration of acid waters a laboratory sieve plate column (according to Aldershaw) with 15 plates of 30 mm diameter is used. As column sump a circulation evaporator provided with an electrically heated heating rod of about 200 ml content, which was fed with a mixture of 70 to 80 wt.% maleic anhydride and 30 to 20 wt.% technical xylene, consisting of 22 vol.% O-xylene, 60 vol.% m-xylene and 18 vol.% p-xylene, was taken. At the top of the column there was installed a reflux condenser and a separation vessel for xylene and water in a way, that the obtained water could be removed continuously. The obtained xylene was led back continuously on the upper column plate. Simultaneously with the xylene led back, acid water reaches over a metering pump the upper column plate. The heating in the column sump was regulated in a way that the formed vapors containing sufficient heating energy to cover the heat for the metered liquid streams the evaporation heat for the water (of acid waters) and the splitting energy (maleic acid to maleic anhydride) as well as the heat losses (by radiation). The metering of the acid water was adjusted on 30 and 35 ml/hour. Corresponding to the yield of maleic anhydride subset was taken from the column sump. The xylene quantity in the system was kept constantly and, if need be, completed by adding small quantities of fresh xylene at the top of the column.

In the described apparatus acid water of the following composition was processed:
 420 g maleic acid/l
 600 mg benzoquinone/l The throughput was 32 ml acid water/hour. Already after a duration of 2 hours a clear discoloration of the column wall in the medium part was observed. After a duration of 17 hours, a clogging occurred which could be removed by water rinse of the column. The discoloration of the walls, however, remained. After a duration of 37, 79, 122, 133 and 165 hours, renewed cloggings occurred which could also be removed by water rinse. The covering at the column wall had expanded over the whole length of the column so that no review was possible. After a duration of 198 hours, a renewed clogging occurred which could not be removed by water rinse.

EXAMPLE 2 (invention)

The apparatus described in Example 1 was fed at the same conditions with acid water which had, after adding phthalic acid, the following composition:
 420 g maleic acid/l
 2 g phthalic acid/l
 600 mg benzoquinone/l The throughput corresponded with that of Example 1. Cloggings occurred after a duration of 11, 35, 108 and 195 hours. It always referred to discolored fumaric acid sediments which could be removed by water rinses. Except for a weak light-brown discoloration of the column walls, no alteration of the column could be observed after the last rinse as compared to the state of the column at the beginning.

What is claimed is:

1. In a process for the preparation of maleic acid anhydride by the dehydration of maleic acid which maleic acid is in an aqueous solution resulting from a catalytic benzene oxidation process and which thus contains benzoquinone, and in which said aqueous maleic acid solution is fed to a distillation zone in which maleic anhydride and an organic solvent are being refluxed and in which the water of dehydration is removed by azeotropic distillation, the improvement for lessening the formation of precipitation products in said distillation zone which comprises adding to the maleic acid aqueous solution, prior to dehydration, 0.1–2.0 wt.% of phthalic acid or its anhydride, based upon the weight of maleic acid.

2. Process according to claim 1 wherein the amount of phthalic acid or its anhydride added to the maleic acid aqueous solution is between 0.2 and 0.5 wt.%.

* * * * *